United States Patent [19]

Lemme et al.

[11] Patent Number: 4,521,516

[45] Date of Patent: Jun. 4, 1985

[54] **STRAIN OF *CLOSTRIDIUM ACETOBUTYLICUM* AND PROCESS FOR ITS PREPARATION**

[75] Inventors: Christopher J. Lemme, Worth; Jeffrey R. Frankiewicz, Lombard, both of Ill.

[73] Assignee: CPC International Inc., Englewood Cliffs, N.J.

[21] Appl. No.: 442,805

[22] Filed: Nov. 18, 1982

[51] Int. Cl.$^3$ .................. C12N 1/20; C12N 15/00; C12N 1/36; C12P 7/26; C12P 7/28; C12P 7/36; C12P 7/34; C12P 7/16; C12R 1/145

[52] U.S. Cl. .................. 435/253; 435/148; 435/150; 435/151; 435/152; 435/160; 435/172.1; 435/245; 435/842

[58] Field of Search .............. 435/150, 157, 160, 172, 435/243, 245, 252, 253, 289, 290, 813, 842, 172.1, 152

[56] References Cited

U.S. PATENT DOCUMENTS

| | | |
|---|---|---|
| 1,315,585 | 9/1919 | Weizmann . |
| 1,822,139 | 9/1931 | Funk .................. 435/150 |
| 2,096,377 | 10/1937 | Loughlin .................. 435/150 |
| 2,198,104 | 4/1940 | Carnarius .................. 435/150 |
| 2,822,319 | 2/1958 | Monod .................. 435/842 |
| 3,361,555 | 1/1968 | Herschler .................. 435/150 |

OTHER PUBLICATIONS

*Advances in Biotechnology*, vol. II: Fuels, Chemicals, Foods, and Waste Treatment, Moo-Young, M. et al, editors, Pergaman Press, New York, pp. 79–83 (1981).
Spivey, M. J., *Process Biochemistry*, vol. 13(11), pp. 2–4, 25, Nov. 1978, "The Acetone/Butanol/Ethanol Fermentation".
Casida, L. E., *Industrial Microbiology*, John Wiley and Sons, Inc., New York, pp. 47, 136–141, 164–171 (1968).
Pirt, S. John, *Principles of Microbe and Cell Cultivation*, John Wiley and Sons, New York, pp. 22–33, 46–56, and 186–193.
*Chemical Abstracts*, vol. 98, pp. 534–535, 1983, Abstract No. 33027r, Van der Westhuizen, et al: "Autolytic Activity and Butanol Tolerance of *Clostridium acetobutylicum*".
*Chemical Abstracts*, vol. 96, p. 531, 1982, Abstract No. 120841d, Andersch, W. et al: "Acetone–Butanol Production by *Clostridium acetobutylicum* in an Ammonium–Limited Chemostat at Low pH Values".
*Chemical Abstracts*, vol. 96, p. 606, 1982, Abstract No. 141151u, Costa, J. M.: "Solvent Toxicity in the Acetone–Butanol Fermentation".
*Chemical Abstracts*, vol. 99, p. 461, 1983, Abstract No. 103607b, Foerberg, C. et al: "Control of Immobilized, Non-Growing Cells for Continuous Production of Metabolites".
*Chemical Abstracts*, vol. 97, p. 463, 1982, Abstract No. 4635m, Bahl, H. et al: "Effect of pH and Butyrate Concentration on the Production of Acetone and Butanol by *Clostridium acetobutylicum* Grown in Continuous Culture".
*Chemical Abstracts*, vol. 93, p. 579, 1980, Abstract No. 6106f, Calam, C. T.: "Isolation of *Clostridium acetobutylicum* Strains Producing Butanol and Acetone".
*Chemical Abstracts*, vol. 71, p. 235, 1969, Abstract No. 90002v, Pomar, F. T.: "Butanol–Acetone Fermentation of Sorghum".
Gottschal, et al, "Continuous Production of Acetone and Butanol by *Clostridium acetobutylicum* Growing in Turbidostat Culture", *Biotechnology Letters*, 4, 477–482 (1982).
Bahl, et al, *European J. Appl. Microbiol. Biotechnol.*, vol. 14 (1982), pp. 17–20.
Jones, et al, *Applied and Environmental Microbiology*, vol. 43 (1982), pp. 1434–1439.
Dyr, et al, "Continuous Cultivation of Microorganisms" (Prague Symposium), pp. 210–226, Prague: Czechoslovakia Academy of Sciences (1958).
Malek, et al, "Theoretical and Methodological Basis of Continuous Culture of Microorganisms", pp. 611–613, Prague: Czechoslovakia Academy of Sciences (1966).
Gottschal, et al, *Biotechnology Letters*, vol. 3 (1981), pp. 525–530.

*Primary Examiner*—Thomas G. Wiseman
*Assistant Examiner*—Jean A. Heck
*Attorney, Agent, or Firm*—Stanley M. Parmerter

[57] ABSTRACT

A novel asporogenic strain of *Clostridium acetobutylicum* is produced by growing a spore-forming strain in a continuous culturing reactor. Culturing is conducted at a dilution rate which prevents accumulation of butanol and acetone in the medium. Culturing at this dilution rate is continued until the asporogenic strain is obtained.

6 Claims, No Drawings

1

STRAIN OF *CLOSTRIDIUM ACETOBUTYLICUM* AND PROCESS FOR ITS PREPARATION

FIELD OF THE INVENTION

This invention relates to an improved strain of *Clostridium acetobutylicum* useful for fermenting carbohydrates to butanol and acetone and to a process for its preparation.

BACKGROUND OF THE INVENTION

The fermentation of carbohydrates to form butanol and acetone by *Clostridium acetobutylicum* (hereafter abbreviated *C. acetobutylicum*) was disclosed by Weizmann in U.S. Pat. No. 1,315,585. For many years, this process was used for the preparation of acetone and butanol, and a certain amount of ethyl alcohol was obtained as a by-product.

Eventually, the microbial process was displaced by chemical processes which provide the same products using cheap fossil fuel row materials. However, the gradual depletion of petroleum fossil fuel with the resultant increase in prices of petrochemical feedstocks has revived interest in this fermentation reaction that uses carbohydrates, which are renewable raw materials.

One problem encountered in production of butanol by the fermentation process is the long time before the microorganism begins to produce appreciable quantities of solvent. This is particularly true if attempts are made to run the reaction in a continuous fermentor. It would therefore be of considerable interest if a strain of microorganism could be developed which would give accelerated batch fermentations or which would reduce the time necessary for the establishment of a steady state of solvent production in a continuous fermentation.

Previous workers have believed that the sporulation of *C. acetobutylicum* is necessary to maintain the organism in an active solvent-producing state. See, for example, Bahl, et al, *European J. Appl. Microbiol. Biotechnol.*, 14, 17-20 (1982). Recently, Jones, et al, *Applied and Environmental Microbiology*, 43, 1434-1439 (1982), reported that certain asporogenic mutants of *C. acetobutylicum* would produce solvents. However, these must be mutants that are still active producers of clostridial forms of cells.

A strain of *C. acetobutylicum* has now been developed which is a good producer of butanol even though it shows little tendency to form spores or to change to clostridial forms. Furthermore, this strain generates butyl alcohol at an accelerated rate in a batch fermentation and reaches a steady state of solvent production in a continuous fermentation in a much shorter time than does the parent strain.

SUMMARY OF THE INVENTION

In accordance with the present invention, there is provided a process for preparing an improved strain of *C. acetobutylicum* which comprises the steps of growing a seed culture from a spore-forming strain of *C. acetobutylicum*, inoculating a growth medium in a continuous culturing reactor with the seed culture, and operating the continuous culturing reactor under conditions of temperature and pH suitable for growth of the microorganism at a dilution rate which prevents accumulation of solvents in the medium for a sufficient time to form a strain that produces more solvents in a shorter time than does the parent strain.

Further in accordance with the present invention, there is provided a biologically pure culture of *C. acetobutylicum*, ATCC 39236 useful for the production of acetone and butanol by fermentation of carbohydrates, characterized in that it has a frequency of reversion to spore formers of less than about $1 \times 10^{-6}$ when grown for 96 hours by a batch process at 35° C. in a medium consisting essentially of an aqueous solution of a 10 D.E. starch hydrolyzate and corn steep liquor.

DETAILED DESCRIPTION OF THE INVENTION

The process of this invention involves conversion of a spore-forming strain of a solvent-producing *C. acetobutylicum* into an asporogenic strain which is a better solvent-producer than the spore-forming parent. This conversion is accomplished by growing the spore-forming strain in a continuous mode at a dilution rate which prevents the buildup of solvents in the medium.

In the description of this invention, the words "dilution rate" designate a value obtained by dividing the flow rate of the medium through the reactor in volume units per hour by the operating volume of the reactor measured in the same volume units. It has the dimensions of per hour.

Any spore-forming strain of *C. acetobutylicum* which forms primarily butanol and acetone by fermentation of carbohydrates can be employed. A particularly useful strain for the practice of this invention is the spore-forming strain of *C. acetobutylicum*, ATCC 4259, which is available from the American Type Culture Collection, Rockville, Md.

The continuous culturing process of this invention is carried out in a medium which comprises an aqueous solution containing dissolved carbohydrates and other nutrients suitable for growth of the microorganism. The medium is sterilized before use by heat or other means well known in the art.

In the practice of this invention, a suitable medium for obtaining the improved strain comprises an aqueous solution of a low D.E. (dextrose equivalent) starch hydrolyzate to which has been added a small amount (from about 0.5% to about 2% by weight, dry basis) of corn steep liquor. Low D.E. (about 5 D.E. to about 20 D.E.) starch hydrolyzates produced by the partial hydrolysis of starch, are readily available from the corn milling industry. Likewise, corn steep liquor, which is produced when corn is soaked in a dilute solution of sulfur dioxide, is available from the corn wet-milling industry.

Continuous culturing is initiated by inoculating the sterile medium in a continuous reactor with a seed culture of the spore-forming strain. A suitable dilution rate for the continuous culturing is from about 0.1 to about 0.5 per hour.

The conditions of pH and temperature used for continuous culturing are those suitable for the growth of the spore-forming microorganism employed. When this microorganism is a strain of *C. acetobutylicum*, a suitable temperature range is from about 34° C. to about 40° C. and a suitable pH is from about 4.5 to about 5.5.

The continuous culturing is carried out at the indicated dilution rate for from about 1 to about 2 weeks until the culture displays asporogenicity. This can be determined by plating the cells of the culture on agar plates containing a suitable growth medium. Cells which grow on these plates in an anaerobic chamber are used to inoculate a liquid growth medium. The cells formed therein are examined microscopically for the presence of spores.

A strain of *C. acetobutylicum*, ATCC 39236, was obtained by the process of this invention. It was isolated from a continuous culture which had been operated according to the process of this invention using an inoculum prepared from the well-known spore-producing strain of *C. acetobutylicum*, ATCC 4259.

Strain ATCC 39236 is designated as an asporogenic strain. The words "asporogenic strain" as used herein designate a strain which has a frequency of reversion to spore formers of less than about $1 \times 10^{-6}$ when grown for 96 hours by a batch process at 35° C. in a medium consisting essentially of an aqueous solution of a 10 D.E. starch hydrolyzate and corn steep liquor.

Surprisingly, Strain ATCC 39236 produces butanol more rapidly and in much better yield than does the parent culture even though the asporogenic strain does not produce clostridial forms which have been thought necessary for the production of solvents. Furthermore, this asporogenic strain reaches a steady state of solvent production in approximately one-fourth of the time required for that of the parent strain when they are used to produce solvents in a continuous fermentation process.

The following examples further describe the embodiments of this invention. All parts are by weight and all percentages are by weight unless expressly stated to be otherwise.

Solvent concentrations were determined using high-performance liquid chromatography (HPLC). Components were analyzed chromatographically by elution with 0.006 N $H_2SO_4$ from a cation-exchange resin in the hydrogen form. The eluted components were detected by means of a differential refractometer, plotted on a recorder and quantitated using an electronic integrator. The area under the curve which represents the concentration of each component is reported as a percentage of the total area. The general procedure is that given in "Analysis of Carbohydrate Mixtures by Liquid Chromatography", *Am. Soc. Brew. Chem. Proc.*, 1973, pp. 43-46. The separations were made on a 1-foot HPX-87 column in the hydrogen form, available from Bio-Rad Laboratories, Richmond, Calif.

EXAMPLE 1

A culture of *C. acetobutylicum*, ATCC 4259, was obtained from the American Type Culture Collection, Rockville, Md., and maintained in a sporulated state on a mixture of soil, sand, and calcium carbonate. Inoculum for initiating a continuous culture was developed in a 125-ml Erlenmeyer seed flask containing 100 ml of an aqueous medium consisting of 10% dry basis of a 10 D.E. starch hydrolyzate (available from the Grain Processing Company, Muscatine, Iowa, as Maltrin M-100) and 1% dry basis of corn steep liquor (available from the Corn Products Unit of CPC International Inc., Englewood Cliffs, N.J., as Code E801). The pH of the medium was adjusted to 6.2 with concentrated NH4OH solution before it was sterilized by heating in an autoclave at 121° C. for 20 minutes. The cooled sterile medium in the seed flask was inoculated with 5 ml of a heat shocked suspension of spores of the culture contained in the same medium. Heat shocking was accomplished by first suspending about 0.5 g of a soil-spore suspension in 10 ml of the seed medium. The suspension was then placed in boiling water for 90 seconds and rapidly cooled to room temperature. The seed flask with inoculated medium was incubated in an anaerobic chamber for 21 hours at 35° C.

A continuous culturing process was conducted in a 2-liter New Brunswick Bioflow, Model C-30 fermentor (New Brunswick Scientific Company, New Brunswick, N.J.) containing a pH controller and a bottom-driven magnetic stirrer. The operating volume of the flask was 1.3 liters. The fermentor was filled with 1200 ml of sterile medium of the same composition as that used to prepare the seed except that it was adjusted to pH 5.0 with concentrated NH4OH. The medium was sparged with $CO_2$ (anaerobic grade) for 30 minutes before it was inoculated with the 100 ml seed culture. The rate of flow of fresh medium into the fermentor was adjusted to give a dilution rate of 0.1 per hour. The mixture was stirred at 200 revolutions per minute (rpm). The temperature was maintained at 37° C., and the pH was controlled at 5±0.1 by the addition of NH4OH as needed. After the continuous culturing process had run for 2 weeks, cells of the culture were plated on Bacto MRS agar plates (Difco Laboratories, Detroit, Mich.) and the plates were incubated at 35° C. in an anaerobic chamber. Within 2 days, colonies of cells appeared. These cells were stored by freezing in glycerin or by lyophilization.

In order to determine frequency of reversion to spore-formers, medium of the same composition as that used to grow the parent culture in this example was inoculated with cells of the asporogenic culture. After 48 hours of growth, no spores were observed in the growth medium. Even after 96 hours of growth, less than 1 in $10^6$ cells contained spores. In contrast, the parent culture when grown in the same medium developed a high concentration ($>10^5$/ml) of spores after 96 hours of growth. This test demonstrates that the strain isolated by the process of this example is asporogenic.

EXAMPLE 2

The procedure of Example 1 was follwed except that the continuous culturing process was run at a dilution rate of 0.28 per hour and at a temperature of 35° C. The asporogenic culture obtained by this method was used to ferment carbohydrates to acetone and butanol by the following batch process. An asporogenic colony was picked from the plate and placed in 100 ml of the starch hydrolyzate/corn steep liquor medium. The culture in this seed flask was grown for 20 hours at 35° C. in an anaerobic incubator. To a sterile solution containing 10% dry basis of a 10 D.E. starch hydrolyzate and 1% dry basis of corn steep liquor adjusted to pH 6.5 with NH4OH was added 0.03% dry basis $CaCO_3$. The mixture was inoculated with 3% by volume of material from the seed flask of the asporogenic culture and fermentation was conducted under anaerobic conditions for 72 hours. A control run was made using as a seed the material from the 21-hour seed flask culture of the present spore-forming strain of *C. acetobutylicum*, ATCC 4259, as described in Example 1. Samples of the fermentation broth were analyzed by HPLC for acetone and butanol after 24, 48 and 72 hours. The results, expressed as grams of solvent per 100 ml of broth in Table I, indicate that the asporogenic culture produces solvents more rapidly and in a much better yield than does the parent culture. Furthermore, this example shows that the strain can produce solvents using only ingredients readily available from the corn wet-milling process.

TABLE I

| Time | Asporogenic Strain | | Parent Strain (Control) | |
|---|---|---|---|---|
| (hrs) | Acetone | Butanol | Acetone | Butanol |
| 24 | — | 0.18 | — | 0.09 |
| 48 | 0.34[a] | 1.02[a] | — | 0.07 |
| 72 | 0.46 | 1.55 | 0.20[b] | 0.53[b] |

[a] At 50 hrs.
[b] At 70 hrs.

EXAMPLE 3

The general batch fermentation process described in Example 2 was followed except that a corn mash medium was used. This medium was obtained by liquefying a 10% dry basis suspension of ground corn in water. Liquefaction was accomplished by adding 2 units of Thermamyl (an alpha-amylase enzyme available from the Novo Enzyme Corporation, Mamaroneck, N.Y.) per gram of corn, heating the mixture for 30 minutes at 90° C., allowing it to cool to room temperature with occasional stirring and then sterilizing it in an autoclave at 121° C. for 20 minutes. An asporogenic colony picked from the plate prepared in Example 1 was used to inoculate a seed flask and the seed was grown as described in Example 2. To 388 ml of sterile corn mash medium was added 12 ml of the suspension of cells from the seed flask and the mixture was allowed to ferment in an anaerobic incubator for 68 hours. A control run was made using as a seed a culture of the parent spore-forming strain of *C. acetobutylicum* prepared as described in Example 1. Samples of the fermentation broth were analyzed by HPLC for acetone and butanol after 20, 44 and 68 hours. The results, expressed as grams of solvent per 100 ml of broth in Table II, indicate that the asporogenic culture produces solvents more rapidly and in much better yield than does the parent culture when both are grown in a corn mash medium.

TABLE II

| Time | Asporogenic Strain | | Parent Strain (Control) | |
|---|---|---|---|---|
| (hrs) | Acetone | Butanol | Acetone | Butanol |
| 20 | 0.07 | 0.06 | — | — |
| 44 | 0.47 | 0.79 | 0.16 | 0.23 |
| 68 | 0.75 | 1.59 | 0.57 | 0.89[a] |

[a] After 5 days, the butanol concentration was 1.3 g/100 ml.

EXAMPLE 4

Two continuous fermentations were run using the medium, seed preparation process, and continuous fermentor as described in Example 1. In one of the fermentations, the culture used was the asporogenic culture obtained in Example 1. In the other fermentation (the control), the culture used was the parent culture of *C. acetobutylicum*, ATCC 4259. Both fermentors were run at a dilution rate of 0.1 per hour and samples of the effluent were analyzed periodically by HPLC for acetone and butanol. The results, expressed as grams of solvent per 100 ml of effluent broth in Table III, indicate that the fermentation run with the asporogenic culture reaches a comparatively steady state of solvent production after 48 hours. In contrast, the parent culture only begins appreciable solvent production after 8 days. It was found that approximately 10 days were required before the parent strain reached a steady state of solvent production. This example shows another unexpected property of the mutant strain of this invention, i.e., it begins to produce solvents in a continuous fermentation much sooner than does the parent culture.

TABLE III

CONTINUOUS FERMENTATION SOLVENT PRODUCTION (g/100 ml)

| Time | Asporogenic Strain | | Parent Strain (Control) | |
|---|---|---|---|---|
| (hrs) | Acetone | Butanol | Acetone | Butanol |
| 24 | — | 0.08 | | |
| 48 | 0.38 | 0.75 | — | 0.04 |
| 72 | 0.20 | 0.41 | — | 0.03 |
| 96 | 0.29 | 0.65 | — | 0.04 |
| 120 | 0.28 | 0.72 | — | 0.07 |
| 144 | 0.23 | 0.63 | — | 0.11 |
| 168 | 0.18 | 0.54 | — | 0.13 |
| 192 | 0.16 | 0.52 | 0.15 | 0.29 |

What is claimed is:

1. A process for preparing an asporogenic strain of *C. acetobutylicum* which comprises growing a seed culture from a spore-forming strain of *C. acetobutylicum*, inoculating a growth medium with the seed culture, and cultivating the inoculated growth medium under continuous conditions at a dilution rate sufficient to prevent accumulation of acetone and butanol in the medium for a sufficient time to form an asporogenic strain, and isolating the asporogenic strain.

2. The process of claim 1 wherein the spore-forming strain of *C. acetobutylicum* is the strain ATCC 4259.

3. The process of claim 1 wherein the cultivation is performed at a temperature of from about 34° to about 40° C.

4. The process of claim 1 wherein the cultivation is performed at a pH of from about 4.5 to about 5.5.

5. The process of claim 1 wherein the dilution rate is from about 0.1 to about 0.5 per hour.

6. A biologically pure culture of *C. acetobutylicum*, ATCC 3923.

* * * * *

UNITED STATES PATENT AND TRADEMARK OFFICE
CERTIFICATE OF CORRECTION

PATENT NO.  : 4,521,516
DATED       : June 4, 1985
INVENTOR(S) : Christopher J. Lemme and Jeffrey R. Frankiewicz It is certified that error appears in the above-identified patent and that said Letters Patent are hereby corrected as shown below:

Column 1, line 21, "row" should read --raw--.

Column 4, line 40, "follwed" should read --followed--.

Column 4, lines 58 and 59, "present" should read --parent--.

Column 6, claim 6, "3923" should read --39236--.

Signed and Sealed this

Third Day of December 1985

[SEAL]

Attest:

Attesting Officer

DONALD J. QUIGG

Commissioner of Patents and Trademarks